US009057093B2

(12) United States Patent
Fovet et al.

(10) Patent No.: US 9,057,093 B2
(45) Date of Patent: Jun. 16, 2015

(54) DETECTION AND ENUMERATION OF MICROORGANISMS

(75) Inventors: Yannick Fovet, Edingen-Neckarhausen (DE); Adrien Ducret, Bloomington, IN (US); Sam Dukan, Marseilles (FR); Marina Periame, Marseilles (FR)

(73) Assignees: BASF SE, Ludwigshafen (DE); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/701,617

(22) PCT Filed: Jun. 1, 2011

(86) PCT No.: PCT/IB2011/052408
§ 371 (c)(1),
(2), (4) Date: Feb. 25, 2013

(87) PCT Pub. No.: WO2011/151793
PCT Pub. Date: Dec. 8, 2011

(65) Prior Publication Data
US 2013/0149739 A1 Jun. 13, 2013

(30) Foreign Application Priority Data
Jun. 3, 2010 (EP) .................................. 10164836

(51) Int. Cl.
C12Q 1/06 (2006.01)
C12Q 1/04 (2006.01)

(52) U.S. Cl.
CPC .. *C12Q 1/06* (2013.01); *C12Q 1/04* (2013.01); *C12Q 1/045* (2013.01)

(58) Field of Classification Search
None
See application file for complete search history.

(56) References Cited

U.S. PATENT DOCUMENTS

| 5,601,998 A * | 2/1997 | Mach et al. ...................... 435/34 |
| 2005/0202518 A1 | 9/2005 | Vedrine et al. |
| 2007/0218522 A1 | 9/2007 | McCoy |
| 2011/0065145 A1 | 3/2011 | Fovet et al. |
| 2011/0076686 A1 * | 3/2011 | Fovet et al. ...................... 435/6 |

FOREIGN PATENT DOCUMENTS

| CN | 101100650 | 1/2008 |
| CN | 101643713 | 2/2010 |
| EP | 1 329 515 | 7/2003 |
| JP | 2006 280219 | 10/2006 |
| WO | 2004 031403 | 4/2004 |
| WO | 2009 121726 | 10/2009 |

OTHER PUBLICATIONS

Fonseca et al., Legionella Molecular Microbiology, Chapter 11: Nutrient Acquisition and Assimilation Strategies of *Legionella pneumophila*, Heuner et al. (Eds.), Published Mar. 1, 2008, Norfolk, UK: Caister Academic Press.*
European Search Report Issued Aug. 16, 2010 Application No. EP 10 16 4836 Filed Jun. 3, 2010.
International Search Report Issued Oct. 27, 2011 in PCT/IB11/052408 Filed Jun. 1, 2011.
Hardy Diagnostics, "Buffered Charcoal Yeast Extract (BCYE) Agar," pp. 1 to 7, (Aug. 13, 2010) XP 002596509.
Tesh, M. J., et al., "Nutritional Requirements of *Legionella-pneumophila* in a Chemically Defined Medium," Absttracts of the Annual Meeting, Total 3 Pages, (Mar. 1 to 6, 1981) XP 009137572.
Tesh, M. J., et al., "Intermediary Metabolism in *Legionella pneumophila*: Utilization of Amino Acids and Other Compounds as Energy Sources," Journal of Bacteriology, vol. 1545, No. 3, pp. 1104 to 1109, (Jun. 1983) XP 002596540.
Diederen, B., et al., "Evaluation of real-time PCR for the early detection of *Legionella pneumophila* DNA in serum samples," Jounal of Medical Microbiology, vol. 56, pp. 94 to 101, (Jan. 2007).
Dutil, S., et al., "Detection of *Legionella* spp. by fluorescent in situ hybridization in dental unit waterlines," Journal of Applied Microbiology ISSN, vol. 100, pp. 955 to 963, (2006).
Delgado-Viscogliosi, P., et al., "Rapid Method for Enumeration of Viable *Legionella pneumophila* and Other *Legionella* spp. in Water," vol. 71, No. 7, pp. 4086 to 4096, (Jul. 2005).
Speck, M. L., et al., "Repair and Enumeration of Injured Coliforms by a Plating Procedure," Applied Microbiology, vol. 29, No. 4, pp. 549 to 550, (1975).
Martin, S., et al., Catalase: Its Effect on Microbial Enumeration, Applied and Environmental Microbiology, vol. 32, No. 5, pp. 731 to 734, (Nov. 1976).
Brewer D., et al., "Beneficial Effects of Catalase or Pyruvate in a Most-Probable-Number Technique for the Detection of *Staphylococcus aureus*," Applied and Environmental Microbiology, vol. 34, No. 6, pp. 797 to 800, (Dec. 1977).
McDonald, L., et al., "Enhanced Recovery of Injured *Escherichia coli* by Compounds That Degrade Hydrogen Peroxide or Block Its Formation," Applied and Environmental Microbiology, vol. 45, No. 2, pp. 360 to 365, (Feb. 1983).

(Continued)

*Primary Examiner* — Karen Cochrane Carlson
*Assistant Examiner* — Jennifer M. H. Tichy
(74) *Attorney, Agent, or Firm* — Oblon, McClelland, Maier & Neustadt, L.L.P.

(57) ABSTRACT

A method for detecting and enumerating viable microorganisms in a sample suspected of containing said microorganisms: (1) contacting said microorganisms of said sample with repair compounds and a growth medium, and (2) incubating the product of step (1), and (3) detecting and enumerating said microorganisms, in which the microorganisms are of the species *Legionella pneumophila*, and in which the repair compounds comprise: (a)serine;(b)threonine;(c)a compound containing calcium ions at a dose of $10^{-6}$ to $10^{-2}$ mM;(d)a compound containing magnesium ions at a dose of $10^{-6}$ to $10^{-2}$ mM;(e)a compound containing potassium ions;(f) glutamic acid or a salt thereof; and (g)pyruvic acid or a salt thereof. The invention also discloses a kit for detecting and enumerating viable microorganisms of the species *Legionella pneumophila* in a sample suspected of containing said microorganisms.

19 Claims, No Drawings

(56) References Cited

OTHER PUBLICATIONS

Marthi, B., et al., "Resuscitation Effects of Catalase on Airborne Bacteria," Applied and Environmental Microbiology, vol. 57, No. 9, pp. 2775 to 2776, (Sep. 1991).

Busch, S., et al., "Development of a Repair-Enrichment Broth for Resuscitation of Heat-Injured *Listeria monocytogenes* and *Listeria innocua*," Applied and Environmental Microbiology, vol. 58, No. 1, pp. 14 to 20, (Jan. 1992).

Dukan, S., et al., "Oxidative Stress Defense and Deterioration of Growth-arrested *Escherichia coli* Cells," The Journal of Biological Chemistry, vol. 274, No. 37, pp. 26027 to 26032, (1999).

Berube, A., et al., "Rapid Detection and Identification of *Legionella pneumophila* by a Membrane Immunoassay," Applied and Environmental Microbiology, vol. 55, No. 6, pp. 1640 to 1641, (Jun. 1989).

Pine, L., et al., "Role of Keto Acids and Reduced-Oxygen-Scavenging Enzymes in the Growth of *Legionella* Species," Journal of Clinical Microbiology, vol. 23, No. 1, (Jan. 1986).

\* cited by examiner

DETECTION AND ENUMERATION OF MICROORGANISMS

This application is a National Stage of PCT/IB11/052408 filed Jun. 1, 2011 and claims the benefit of EP 10164836.8 filed Jun. 3, 2010.

The present invention concerns a method for detecting and enumerating viable microorganisms of the species *Legionella pneumophila* in a sample. The invention also includes a kit suitable for use in such a method. This method and kit enable viable microorganisms to be quantified more rapidly.

*Legionella* bacteria are ubiquitous in wet or moist environments such as soil and non-marine aquatic habitats. They can also be found in warm and cold water installations, cooling towers of air conditioning systems and water humidifiers.

*Legionella*, especially *Legionella pneumophila*, are pathogens that can cause an acute bacterial pneumonia, generally known as "legionnaires disease", which is often lethal for infected individuals.

Traditionally detection and enumeration of *Legionella pneumophila* are achieved by cell culturing. This method may be achieved by measuring culturable bacteria using plate count or measuring micro-colonies employing a filter membrane method. These techniques evaluate viable bacteria by their ability to form a colony or micro-colony. Unfortunately, such methods usually require between 3 and 10 days in order to allow the colonies or micro-colonies to form. Where water installations are still in operation there is an unacceptable risk of human infection during this time.

Other methods for detecting total *Legionella* microorganisms include PCR (Polymerase Chain Reaction) techniques. PCR employs DNA polymerase to amplify a piece of DNA by in vitro enzymatic replication. During the progression of the technique the DNA generated is used as a template for replication which brings about a chain reaction in which the DNA template is exponentially amplified. PCR enables a single or few copies of a piece of DNA to be amplified by generating millions or more copies of the DNA piece. Typically such a method is described by Diederen et al., J Med Microbiol. 2007 January; 56 (Pt 1):94-101.

However a drawback of PCR is that the samples tend to contain polymerisation reaction inhibitors and therefore do not consistently provide quantitative results. Furthermore, the technique relies upon a prior DNA purification step which can result in loss of DNA with the consequential underestimation of the *Legionella* present. To some extent these disadvantages are overcome by real-time PCR which is quantitative. However, the technique cannot distinguish between viable cells and non-viable cells.

Another technique is fluorescent in situ hybridisation (FISH) in which an oligonucleotidic probe labelled by a fluorescent substance penetrates into the bacteria cells. Where the ribosomal nucleic acids (rRNA) have the correct sequence to the probe known as the target, the probe will attach itself to its target and will not be removed by any subsequent washing step. The bacteria in which the probe is fixed will then emit a fluorescent signal. This fluorescent signal may then be quantified by techniques such as flow cytometry, solid phase cytometry, or epifluorescent microscopy. A typical FISH technique is described by Dutil S et al J Appl Microbiol. 2006 May; 100(5):955-63. However, using the FISH technique alone the total number of viable *Legionella pneumophila* could be detected but unfortunately the method could not exclusively identify only those *Legionella pneumophila* bacteria able to divide and by consequence make a colony.

A further method for enumerating viable *Legionella pneumophila* involves Chem-Chrome V6 and is described by Delgado-Viscogliosi et al Appl Environ Microbiol. 2005 July; 71(7):4086-96. This method allows the quantification of *Legionella pneumophila* as well as discrimination between viable and non-viable bacteria. It combines specific detection of *Legionella* cells using antibodies and a bacterial viability marker (Chem-Chrome V6) and employing epifluorescent microscopy for the enumeration. However, although this technique distinguishes between viable and non-viable cells it is not able to separately identify those colony-forming bacteria.

US 20070218522 describes methods and compositions for detecting and quantifying viable *Legionella* and other heterotrophic aerobic bacteria the method includes the use of dipslides that include an absorbent medium, growth promoting and growth selective substances for rapid detection and quantification of micro-colonies of *Legionella*. This technique would not enumerates injured bacteria.

EP 1329515 relates to a method of testing for the presence of microorganisms in a gaseous environment comprising hydrogen peroxide by bringing the gaseous environment into contact with an agar growth medium comprising a salt of pyruvic acid and allowing the development of colonies of the microorganisms.

Techniques which involve the growth of colonies on a growth medium, such as a nutrient agar plate, are generally considered to be more accurate. Consequently the plate count method remains the preferred choice of method for obtaining the total viable count. This generally means applying a sample suspected of containing the microorganism onto a plate containing a solid nutrient source or growth medium. Such a technique is generally referred to as plating. By total viable count we mean the total number of bacteria capable of yielding a population discernible by the observer. Typically this will mean a visible colony on the surface of a growth medium such as nutrient agar plate.

However, microorganisms such as *Legionella pneumophila* in the environment may be subject to one or more stresses which prevent the microorganism from growing and multiplying in its environmental situation. Such stressed microorganisms would not divide at all or form a visible colony under normal culturing conditions. In the environment a proportion of microorganisms cells will generally be stressed due to environmental conditions, such as starvation, presence of biocide, heat shock and desiccation. Furthermore, these cells may be in a vulnerable physiological state in which the technique of plating the microorganisms may exacerbate stressing of those already stressed microorganisms cells due to the presence of atmospheric oxygen. Furthermore this could lead to artifactual death of the stressed bacteria leading to an underestimation of the total viable count.

In addition, underestimation of viable *Legionella pneumophila* with plating method might become hazardous in regard to its pathogenicity.

Since the 1970s it has been reported that scavengers of reactive oxygen species (ROS) should be used to limit the effect of oxidative stress during the plating process. This was reported by Speck et al, repair and enumeration of injured coliforms by a plating procedure, Appl Microbiol 29, 549-50 (1975); Martin et al Catalase: its effect on microbial enumeration. Appl Environ Microbiol 32, 731-4 (1976); Brewer et al Beneficial effects of catalase or pyruvate in a most-probable-number technique for the detection of *Staphylococcus aureus*. Appl Environ Microbiol 34, 797-800 (1977); McDonald et al, Enhanced recovery of injured *Escherichia coli* by compounds that degrade hydrogen peroxide or block its formation. Appl Environ Microbiol 45, 360-5 (1983); Marthi et al) Resuscitation effects of catalase on airborne bacteria.

Appl Environ Microbiol 57, 2775-6 (1991); Busch and Donnelly Development of a repair-enrichment broth for resuscitation of heat-injured *Listeria monocytogenes* and *Listeria innocua*. Appl Environ Microbiol 58, 14-20 (1992); and Dukan et al, Oxidative stress defense and deterioration of growth-arrested *Escherichia coli* cells. J Biol Chem 274, 26027-32 (1999).

However, in all the aforementioned cases the inventors of the present invention believe that the ROS would be reduced by a direct route in which the compound reacts chemically with ROS.

Bérubé et al, "Rapid detection and identification of *Legionella pneumophila* by membrane immunoassay", Applied and Environmental Microbiology, 1989, 55, 1640-1641 describes the detection and identification of *Legionella pneumophila* by an immunoblot assay using a monoclonal antibody. No means is provided for dealing with the problem of injured bacteria.

An article by Pine et al (Role of keto acids and reduced-oxygen-scavenging enzymes in the growth of *Legionella* species. J Clin Microbiol 23, 33-42 (1986)) describes the necessity for the addition of keto acids and reduced oxygen scavenging enzyme is to optimise the growth of *Legionella pneumophila* and suggested using these materials in the medium used for standard enumeration of this microorganism.

However the use of keto acids and reduced oxygen scavenging enzyme alone is insufficient to repair the stressed *Legionella pneumophila* cells to be repaired and allow accurate enumeration. This is especially so when using a specific growth medium for *Legionella pneumophila*, such as buffered charcoal yeast extract (BCYE) agar medium. In fact, there is no data available concerning the optimisation of a standard medium useful for the accurate enumeration of *Legionella pneumophila*.

WO 2009 121726 describes a method for detecting and enumerating viable *Legionella pneumophila* microorganisms in a sample by contacting the microorganisms with at least one repair compound and a growth medium followed by the steps of incubation and detecting and quantifying viable microorganisms. The repair compound directly or indirectly causes an effect on the metabolism to reduce the oxidative stress of the microorganism. There is repair compounds are suggested including pyruvate and glycolic acid. The method provides an excellent means for more accurately enumerating viable *Legionella pneumophila* within a shorter time span than previous methods.

However, it would be desirable to provide an improved method for even more accurately enumerating viable *Legionella pneumophila* and even more rapidly. Furthermore, it would also be desirable to achieve this across a broader spectrum of strains of *Legionella pneumophila*.

Thus according to the present invention we provide a method for detecting and enumerating viable microorganisms in a sample suspected of containing said microorganisms (1) Contacting said microorganisms of said sample repair compounds and a growth medium, and
(2) Incubating the product of steps (1), and
(3) Detecting and quantifying said viable microorganisms, in which the microorganisms are of the species *Legionella pneumophila*,
and in which the repair compounds comprise
(a) serine;
(b) threonine;
(c) a compound containing calcium ions at a dose of $10^{-6}$ to $10^{-2}$ mM;
(d) a compound containing magnesium ions at a dose of $10^{-6}$ to $10^{-2}$ mM;
(e) a compound containing potassium ions.
(f) glutamic acid or a salt thereof,
and
(g) pyruvic acid or salt thereof.

We have found that the use of these compounds in conjunction as a repair compounds in the present method significantly the latency period of the *Legionella pneumophila* microorganisms is significantly reduced. In fact we have found that this is achieved across a wider spectrum of *Legionella pneumophila* strains.

Without being limited to theory it is believed that the combination of pyruvate, glutamate and the specific concentrations of calcium and magnesium ions that bring about it beneficial effect in directly or indirectly removing or reducing oxidative stress and it is thought that the potassium ions decrease osmotic shock whilst the serine and threonine enhance the metabolism. It is believed that this special combination of repair compounds provides a synergistic improvement in removing or reducing oxidative stress, decreasing osmotic shock and enhancing the metabolism thereby achieving the objectives of the present invention.

In the invention the desired dose of serine or threonine can be between 0.01 and 5% based on weight of repair compound on volume of sample. Desirably this will be usually in the range of between 0.05 and 2.5%, for instance between 0.1 and 2%, often between 0.5 and 1%. Glutamic acid (or salt thereof) and/or pyruvic acid (or salt thereof) are used at a desired dose of between 0.01 and 5% based on weight of repair compound on volume of sample. Desirably this will be often between 0.05 and 2.5%, for instance between 0.1 and 2%, frequently in the range of 0.5 and 1%.

Each of the compounds containing the calcium ions, magnesium ions or potassium ions may be any suitable salts. Desirably they should be water-soluble at least sufficiently to allow the required dose. The salts may have any suitable counterions. The skilled person would in any case realise that the counterions should not be known toxins for microorganisms such as *Legionella pneumophila*. Typically the counterions will include but not be limited to chloride, sulphate, nitrate etc.

As indicated above when the compound contains calcium ions it should be used at a dose of $10^{-6}$ to $10^{-2}$ mM, preferably this will be within the range of $10^{-5}$ to $10^{-3}$ mM, more preferably $5\times10^{-4}$ $5\times10^{-3}$, especially around $10^{-4}$. With regard to a compound containing magnesium ions as indicated above the dose should be $10^{-6}$ to $10^{-2}$ mM, preferably this will be within the range of $10^{-5}$ to $10^{-3}$ mM, more preferably $5\times10^{-4}$ to $5\times10^{-3}$ mM, especially around $10^{-4}$ mM.

The repair compound containing potassium ions desirably should be used at a dose that can be 1 to $10^{-4}$ mM, for example between $10^{-1}$ to $10^{-3}$ mM, more preferably between $5\times10^{-1}$ to $5\times10^{-2}$ mM, especially around $10^{-2}$ mM.

The repair compounds are used in conjunction which means they may be used simultaneously or sequentially. By sequentially we mean adding each compound substantially one after the other. By simultaneously we mean adding that two or more repair compounds to the sample at the same time. It may also be desirable to combine the two or more of the repair compounds into a formulation and thereby negating separate additions of the repair compounds.

We believe that the repair compounds pyruvate, glutamate, calcium containing and magnesium act directly or indirectly on the metabolism of the microorganism in a way that reduces the oxidative stress of the microorganism. In this way we believe that the pyruvate, glutamate, calcium containing and magnesium containing repair compounds act endogenously on the microorganisms.

By oxidative stress we mean an imbalance between the concentration of ROS (endogene production or exogene adduction) and the ability of the microorganisms to readily detoxify the reactive intermediates or efficiently repair the resulting damage. Such disruption of the normal metabolic processes of the microorganism can cause toxic effects due to the formation of free radicals and oxidising agents, such as peroxides, which may lead to damage to the components of the microorganisms cells, for instance DNA, proteins or lipids.

Causing an effect on the metabolism of the microorganism means bringing about changes to natural internal chemical processes within the microorganism cell.

Reference to endogenously means changes are brought about within the microorganism cell to reduce oxidative stress. This could for instance be changes to the metabolic processes within the microorganism. It may also include removal of ROS within the microorganism cell.

Furthermore, it is believed that the pyruvate, glutamate, calcium ions and magnesium ions may directly or indirectly inhibit the formation of and/or degrades the ROS. Such a compound that exerts an indirect effect on the ROS may do this by interfering with the metabolism of the microorganism. Such a combination of repair compounds may be regarded as indirectly reducing ROS endogenously for instance during aerobic respiration.

The potassium compounds help to reduce osmotic shock. By osmotic shock we mean the imbalance of solute concentration between the environment surrounding a cell and inside the cell. This imbalance causes a rapid change in the movement of water across cell membrane and could lead to cell damage. Injured cells or altered cell are much more sensitive to osmotic stress and could lose viability due this type of stress.

The serine and threonine are believed to modify the metabolism of the microorganism. By this we mean that serine and threonine are involved in a metabolic pathway that is believed to directly or indirectly induce an enhanced metabolic rate in cells that have a limited or reduced metabolism. Using these two molecules cells were able to exhibit improved growth.

Desirably the aforementioned combination of repair compounds according to the present invention synergistically improve the combination of reducing or removing ROS, reducing osmotic shock and improving metabolism. This is especially true of a wider spectrum *Legionella pneumophila* strains than previously possible.

We have found that the present method induces the repair of stressed *Legionella pneumophila* cells across a wider spectrum of *Legionella pneumophila* strains and thus more accurately provides a total viable count. Unexpectedly we have also found that the method further reduces the amount of incubation time required. In general we find that the method can reduce the incubation time by many hours and in some cases at least one or two days.

Unexpectedly we have also found that the inventive method can bring about a reduction of interfering microorganisms i.e. those microorganisms other than the *Legionella pneumophila*.

The method of the present invention which suitably involves contacting stressed *Legionella pneumophila* microorganism cells with combination of the repair compounds according to the present invention desirably inhibits the formation of and/or reduces and/or removes ROS reduces osmotic shock and improves metabolism and this tends to induce repair of the stressed cells.

The *Legionella pneumophila* microorganism may be brought directly in contact with the repair compound upon collection of the sample. Thus the container into which the sample of water, believed to contain the microorganism, is collected may already contain the repair compounds. Alternatively once a sample of water containing the *Legionella pneumophila* has been collected it may be diluted with dilution water containing repair compounds for analysis purpose. In a further alternative the sample, optionally having been diluted, may be brought into contact with the growth medium containing the repair compounds or the repair compounds may be applied after contacting the microorganism with the growth medium. Once the sample has been collected it may be desirable to put this into storage until it is convenient to carry out the method according to the present invention. It may be desirable to incorporate all of the repair compounds during storage.

Preferably all of the repair compounds used in conjunction according to the present invention should be brought into contact with the microorganisms during the dilution step or during storage of the sample.

One form of this invention desirably involves contacting said sample with a repair medium, preferably a non-selective repair medium, containing said repair compound and then bringing this into contact with a growth medium, preferably a selective growth medium. Preferably the repair medium is a liquid and more preferably a broth. Where the repair medium is a liquid this is suitably referred to as a liquid repair method. Typically in a liquid repair method the sample is first introduced into a liquid medium containing the combination of according to the present invention. Ideally the liquid repair method allows stressed bacteria to repair in a non-selective liquid medium. Preferably the liquid repair method will employ a broth as the liquid medium. In general the liquid medium containing the *Legionella pneumophila* microorganisms will then be transferred to a growth medium. The stressed microorganisms would either have been repaired prior to transference to the growth medium or would repair upon contact with the growth medium. More preferably the growth medium is a selective growth medium. Typically the liquid medium containing the microorganisms will be plated onto a selective growth medium plate such as a selective agar growth medium plate.

In an alternative preferred form step (1) comprises contacting said sample with a growth medium, preferably a non-selective growth medium containing said combination of repair compounds, and then bringing this into contact with a repair medium also containing said repair compound. Preferably the repair medium is a non-selective repair medium, more preferably a solid, and particularly preferably a selective agar growth medium. When the repair medium is a solid this is would be termed a solid repair method. Typically the solid repair method will involve contacting the sample with a non-selective growth medium containing the combination of repair compounds according to the present invention. Subsequently this can be brought into contact with a selective growth medium containing the repair compound or combination of repair compounds. In this form the selective ingredients and the compound or compounds, which prevents the formation, reduces or removes the ROS, will defuse across into the non-selective medium. Desirably the non-selective growth medium can be a non-selective agar growth medium. Suitably in this form the sample can be plated onto any non-selective agar and then a selective agar growth medium containing the compound or compounds that prevent the formation, reduces or removes the ROS is overlaid onto the non-selective agar growth medium.

In a further alternative form the sample may be applied to a selective growth medium which already contains the combination of repair compounds. Such a selective growth medium may be a selective agar growth medium. Plating of the sample may be carried out as described previously.

In a further alternative form the sample may be collected from water in the form of an aerosol. Typically the aerosol may be located in a cooling tower or air conditioner. Desirably the water condensed from the aerosol before testing according to the method of the present invention. In an alternative preferred form step (1) comprises contacting said sample from aerosol with a dilution water containing a repair medium, preferably a non-selective repair medium containing said combination of repair compounds, and then bringing this into contact with a growth medium also containing said combination of repair compounds.

In all of the aforementioned forms of the invention the growth medium should be suitable for growth of *Legionella pneumophila*. Suitable growth medium types are documented in the literature and are well known to the skilled person. Normally the growth medium should contain activated carbon and cysteine.

It is preferred that the selective growth medium is a selective agar growth medium and more preferably is a buffered charcoal yeast extract (BCYE) agar growth medium. The BCYE growth medium would become selective by the addition of antibiotic supplement. A highly desirable BCYE growth medium with antibiotic is known as GVPC (Glycine, Vancomycine, Polymyxine B, Cycloheximide).

The plating method is documented in the literature and is well known that the skilled person. Typically the method will involve applying a quantity of these samples of water onto agar gel that has been placed in a Petri dish. This may be termed a Petri dish method or an agar plating method. The aim of the agar plating is to spread an aliquot, typically 100 μl of water suspected of containing the microorganism, termed a bacterial suspension, onto a solid medium in a Petri dish. Glass beads or a cell scraper can be used to spread the bacterial suspension on the agar plate. After spreading, most of the liquid is absorbed by the agar and a thin layer with bacteria remains on the agar surface. By incubation, bacterial growth in the form of colonies developed on the agar surface. The incubation will occur at a temperature best suited for the microorganism, which is well documented in the literature and known to the skilled person. Typically the temperature will be between 30° C. and 50° C., for instance around 37° C.

The combination of repair compounds should be added in an amount effective to reduce oxidative stress of the microorganism. Preferably this will be an amount effective to reduce or substantially remove ROS in the microorganism cell.

In fact we have found that using a combination of repair compounds brings about a significant reduction of lag phase during development of the *Legionella pneumophila*, in particular in a liquid medium. Such a reduction of lag phase in liquid medium results in a reduction of the time required to obtain a visible colony on agar plate.

It may also be desirable to include a keto acid and/or a reduced oxygen scavenging enzyme with the repair medium and/or growth medium. A keto acid and/or a reduced oxygen scavenging enzyme are not considered a repair compound according to the present invention. Nevertheless, it may be beneficial to include one or both of these compounds with any of the aforementioned combination of repair compounds.

Detecting and quantifying the viable microorganisms can be carried out by any of the known technique which is documented in the literature. Typically this will mean counting the visible colonies of the surface of the growth medium, such as nutrient agar plate.

The method according to present invention facilitates the accurate quantitative determination for the existence of *Legionella pneumophila*. Furthermore, the incubation time may be significantly reduced. The method is suitable for detecting *Legionella pneumophila* in samples derived from any of the group selected from industrial cooling waters, drinking waters, and natural waters.

The present invention also incorporates a kit for more accurately detecting and enumerating viable microorganisms of the species *Legionella pneumophila* in a sample suspected of containing said microorganisms comprising:
(1) repair compounds,
(2) a growth medium,
(3) a means for incubation
(4) a means for detecting and quantifying the microorganisms, in which the microorganisms are of the species *Legionella pneumophila*, and in which the repair compounds comprise
(a) serine;
(b) threonine;
(c) a compound containing calcium ions;
(d) a compound containing magnesium ions;
(e) a compound containing potassium ions.
(f) glutamic acid or a salt thereof,
and
(g) pyruvic acid or salt thereof.

The kit may also contain any of the embodiments described in regard to the first aspect of the invention.

The kit is suitable for use with the method of the present invention and enables more accurate enumeration of *Legionella pneumophila*, especially with regard to a wider spectrum of *Legionella pneumophila* strains.

The following examples illustrate the invention.

EXAMPLES

Selection of Compounds and Determination of their Optimal Concentrations

In order to measure the effects of different compounds, 2 criteria are compared: the latency and the growth rate are observed with the culture medium and the supplemented medium unsupplemented culture. For simplicity, the latency is estimated by time necessary to obtain an optical density of 0.1 at 600 nm. For all compounds tested, the gain of latency (denoted by GT) is obtained by difference between the latencies obtained on the reference medium (YEC) and obtained on medium supplemented. In the same conditions, the ratio of growth rate (denoted RVC) is defined as the ratio between the growth rate obtained on the reference medium and that obtained on medium supplemented (YEC+X). In reference medium (YEC), the strains of *L. pneumophila* have a time lag between 5 h and 15 h and require about 10 hours in order to reach an optical density (denoted as OD) between 0.1 and 0.3.

When using serine or threonine as the repair compounds in each case improvements in latency and/or growth rate are observed for a variety of *Legionella pneumophila* strains. Improvements are seen over a range of doses, for instance between 0.01 and 5% based on weight of compound on volume of sample with the optimal dose around 1 g per litre.

Improvements in latency and/or growth rate are observed for numerous *Legionella pneumophila* strains when using calcium chloride or magnesium chloride at doses of between $10^{-6}$ to $10^{-2}$ mM, especially $10^{-4}$ mM.

Improvements in latency and/or growth rate are observed for a number of *Legionella pneumophila* strains when using potassium chloride at doses of between 1 to $10^{-4}$ mM, especially around $10^{-2}$ mM.

Particularly effective combinations of repair compounds include:

Combination A 1 g per litre pyruvate, 1 g per litre serine, 1 g per litre threonine, 1 g per litre glutamic acid, $10^{-4}$ mM calcium chloride, $10^{-4}$ mM magnesium chloride.

Combination B 1.5 g per litre pyruvate, 1.5 g per litre serine, 1.5 g per litre threonine, 1 g per litre glutamic acid, $10^{-4}$ mM calcium chloride and $10^{-4}$ mM magnesium chloride.

Combination C 2 g per litre pyruvate, 2.5 g per litre serine, 1 g per litre threonine, 1 g per litre glutamic acid, $10^{-4}$ mM calcium chloride, $10^{-4}$ mM magnesium chloride and $1.16 \times 10^{-2}$ mM potassium chloride.

The results will show that several combinations are beneficial to the growth specially in liquid medium containing different strains.

The invention claimed is:

1. A method for detecting and enumerating a viable microorganism in a sample comprising the microorganism, the method comprising:
   (1) contacting the microorganism of the sample with a repair compound and a growth medium to obtain a product,
   (2) incubating the product (1), and
   (3) detecting and quantifying the viable microorganism in the product,
   wherein the microorganism is a species of *Legionella pneumophila*, and wherein the repair compounds are:
   (a) 0.01 to 5% weight/volume of serine;
   (b) 0.01 to 5% weight/volume of threonine;
   (c) a compound comprising a calcium ion at a dose of $10^{-6}$ to $10^{-2}$ mM;
   (d) a compound comprising a magnesium ion at a dose of $10^{-6}$ to $10^{-2}$ mM;
   (e) optionally a compound comprising a potassium ion;
   (f) 0.01 to 5% weight/volume of glutamic acid or a salt thereof; and
   (g) 0.01 to 5% weight/volume of pyruvic acid or a salt thereof.

2. The method according to claim 1, wherein contacting (1) comprises contacting the sample with a repair medium comprising the repair compound, to obtain an intermediate product and then further contacting the intermediate product with the growth medium.

3. The method according to claim 2, wherein the repair medium is a liquid.

4. The method according to claim 1, wherein contacting (1) comprises contacting the sample with the growth medium to obtain an intermediate product, and then contacting the intermediate product with a repair medium comprising the repair compound.

5. The method according to claim 2, wherein the repair medium is a selective repair medium.

6. The method according to claim 1, wherein contacting (1) comprises contacting the sample with the growth medium comprising the repair compound.

7. The method according to claim 1, wherein the growth medium is a buffered charcoal yeast extract or an agar growth medium.

8. The method according to claim 2, wherein the repair medium, the growth medium, or both, further comprise a keto acid, a reduced oxygen scavenging enzyme, or any mixture thereof.

9. A kit for more accurately detecting and enumerating a viable microorganism of the species *Legionella pneumophila* in a sample comprising the microorganism comprising:
   (1) repair compounds,
   (2) a growth medium,
   (3) a means for incubation, and
   (4) a means for detecting and quantifying the microorganism,
   wherein the microorganism is of the species *Legionella pneumophila*, and wherein the repair compound comprises:
   (a) 0.01 to 5% weight/volume of serine;
   (b) 0.01 to 5% weight/volume of threonine;
   (c) a compound containing a calcium ion;
   (d) a compound containing a magnesium ion;
   (e) optionally a compound containing a potassium ion;
   (f) 0.01 to 5% weight/volume of glutamic acid or a salt thereof; and
   (g) 0.01 to 5% weight/volume of pyruvic acid or a salt thereof.

10. The method according to claim 1, wherein the
   the compound comprising a calcium ion is present at a dose of $10^{-5}$ to $10^{-3}$ mM; and
   the compound comprising a magnesium ion is present at a dose of $10^{-5}$ to $10^{-3}$ mM.

11. The method according to claim 1, wherein
   the compound comprising a calcium ion is present at a dose of $5 \times 10^{-4}$ to $5 \times 10^{-3}$ mM; and
   the compound comprising a magnesium ion is present at a dose of $5 \times 10^{-4}$ to $5 \times 10^{-3}$ mM;

12. The method according to claim 1, wherein
   the compound comprising a calcium ion is present at a dose of $10^{-4}$ mM; and
   the compound comprising a magnesium ion is present at a dose of $10^{-4}$ mM.

13. The method according to claim 2, wherein the repair medium is a non-selective repair medium comprising the repair compound.

14. The method according to claim 2, wherein the growth medium is a selective growth medium.

15. The method according to claim 3, wherein the repair medium is a broth.

16. The method according to claim 4, wherein the growth medium is a non-selective growth medium.

17. The method according to claim 5, wherein the repair medium is a solid.

18. The method according to claim 5, wherein the repair medium is a selective agar growth medium.

19. The method according to claim 5, wherein the compound comprising a potassium ion is included as a repair compound.

\* \* \* \* \*